(12) United States Patent
Boehm et al.

(10) Patent No.: US 12,728,378 B2
(45) Date of Patent: Sep. 8, 2026

(54) DEHYDROGENATION AND PYROLYSIS PRODUCT RECOVERY WITH HEAT INTEGRATION

(71) Applicant: UOP LLC, Des Plaines, IL (US)

(72) Inventors: Ernest J. Boehm, Hanover Park, IL (US); Sudipta K. Ghosh, Gurgaon (IN); Prashant Balyan, Gurgaon (IN); Xin X. Zhu, Long Grove, IL (US); Kyle Cuellar, Fulshear, TX (US)

(73) Assignee: UOP LLC, Rosemont, IL (US)

( * ) Notice: Subject to any disclaimer, the term of this patent is extended or adjusted under 35 U.S.C. 154(b) by 236 days.

(21) Appl. No.: 18/510,311

(22) Filed: Nov. 15, 2023

(65) Prior Publication Data

US 2024/0165551 A1 May 23, 2024

Related U.S. Application Data

(60) Provisional application No. 63/384,932, filed on Nov. 23, 2022.

(51) Int. Cl.
*B01D 3/14* (2006.01)
*B01D 53/00* (2006.01)
*C07C 4/04* (2006.01)
*C07C 5/327* (2006.01)
*C07C 7/09* (2006.01)

(52) U.S. Cl.
CPC ........... *B01D 53/002* (2013.01); *B01D 3/143* (2013.01); *B01D 2256/24* (2013.01); *B01D 2257/108* (2013.01); *C07C 4/04* (2013.01); *C07C 5/327* (2013.01); *C07C 7/09* (2013.01)

(58) Field of Classification Search
CPC ......... Y10S 203/04; B01D 3/007; B01D 3/14; B01D 203/27; B01D 203/94; B01D 203/98; B01D 203/99; B01D 585/80
See application file for complete search history.

(56) References Cited

U.S. PATENT DOCUMENTS 3,336,761 A * 8/1967 Mcharg .................... B01D 3/14 62/623
6,244,070 B1 * 6/2001 Lee ........................ F25J 3/0209 62/620
2002/0042550 A1 4/2002 Pironti et al.
(Continued)

FOREIGN PATENT DOCUMENTS

CN 210569512 U * 5/2020
WO 2020163047 A1 8/2020

OTHER PUBLICATIONS

Hirata, K. Energy Saving for Ethylene Process by Advanced Integration, Apr. 2011, Chem Eng Trans 25, [retrieved on Aug. 22, 2025]. Retrieved from Internet < https://skoge.folk.ntnu.no/prost/proceedings/pres2011-and-icheap10/PRES11/6Hirata.pdf> (Year: 2011).*

(Continued)

*Primary Examiner* — Elizabeth J Martin
*Assistant Examiner* — Keona Lauren Banks
(74) *Attorney, Agent, or Firm* — Paschall & Associates, LLC; James C. Paschall

(57) ABSTRACT

A process and apparatus integrate recovery of propylene from a pyrolysis reactor and a paraffin dehydrogenation reactor. The improved process for recovering light olefins utilizes heats of compression to heat reboil streams.

16 Claims, 3 Drawing Sheets

(56) References Cited

U.S. PATENT DOCUMENTS

| | | | | |
|---|---|---|---|---|
| 2004/0182752 | A1 | 9/2004 | Reyneke et al. | |
| 2008/0141712 | A1* | 6/2008 | Verma | F25J 3/0242 62/620 |
| 2008/0302650 | A1* | 12/2008 | Bello | F25J 3/0209 203/25 |
| 2009/0120780 | A1* | 5/2009 | Wegerer | C07C 7/04 202/158 |
| 2021/0171836 | A1* | 6/2021 | Purola | C10G 9/24 |
| 2022/0316798 | A1 | 10/2022 | Cuellar et al. | |

OTHER PUBLICATIONS

Jana, A. Advances in heat pump assisted distillation col. A review, Jan. 2014, Energy Conversion and Management, vol. 77 [retrieved on Aug. 23, 2025]. Retrieved from Internet <DOI: https://doi.org/10.1016/j.enconman.2013.09.055 >) (Year: 2014).*
Yang (CN210569512U) English Translation (Year: 2020).*
Search Report and Written Opinion for PCT/US2023/080920 dated Mar. 20, 2024.

* cited by examiner

DEHYDROGENATION AND PYROLYSIS PRODUCT RECOVERY WITH HEAT INTEGRATION

FIELD

The field relates to recovery of light olefins, ethylene and propylene, and also recovery and separation of light component by-products such as hydrogen, methane, ethane and propane. Particularly, the field relates to recovery of ethylene and propylene from pyrolysis effluent and dehydrogenation effluent.

BACKGROUND

Dehydrogenation of propane and steam cracking of saturated and predominantly paraffinic hydrocarbons such as naphtha, butanes, propane and ethane are important commercial hydrocarbon conversion processes because they produce light olefins which are building blocks for polyolefins and polymers whose demand is growing. In particular, demand of ethylene and propylene in the petrochemical industry has grown substantially due to their use as precursors in the production of polyethylene and polypropylene for many commercial products. One route for producing propylene is the dehydrogenation of propane. The main products from a steam cracker are ethylene and propylene; however other byproducts such as hydrogen, methane and other heavier hydrocarbons may be further processed for other petrochemical processes.

A process for the conversion of paraffins to olefins via propane dehydrogenation process involves passing a propane feed stream over a highly selective catalyst to dehydrogenate the propane to propylene in the dehydrogenation reactor effluent. Cooling and separation of the dehydrogenation reactor effluent into a hydrocarbon-rich fraction and a hydrogen-rich vapor fraction, part of which is non-recycled net gas, is provided in a cryogenic separation system that requires refrigeration for cooling the process streams in order to separate hydrogen from light hydrocarbon liquid. The conventional cryogenic separation system cools process streams alone to remove hydrogen from light hydrocarbon. However, further fractionation is needed to separate the C2− material from the C3 hydrocarbons in the dehydrogenation effluent in a deethanizer column which also typically requires a refrigeration package.

The great bulk of the ethylene consumed in the production of plastics and petrochemicals such as polyethylene is produced by thermal cracking or pyrolysis of hydrocarbons. Pyrolysis also produces substantial propylene that is useful in the plastics industry for making polypropylene. Steam is usually mixed with the feed stream to the cracking furnace to reduce the hydrocarbon partial pressure and enhance olefin yield and to reduce the formation and deposition of carbonaceous material in the cracking reactors. The process is therefore often referred to as steam cracking or pyrolysis.

Steam cracking generates lower value by-products such as pyrolysis gasoline (pygas) and fuel oil (pyoil). Pygas contains large proportions of paraffins and aromatics. The resulting paraffins include normal and non-normal paraffins which can be recovered or further processed. Aromatics are very stable and difficult to crack in a steam cracker. The paraffinic side chains can be removed, but this leads to the production of multi-ring aromatics which increases the yield of low-value fuel oil. Normal paraffins more selectively pyrolyze to olefins than non-normal paraffins.

Improvements in separation systems are necessary to recover propylene from dehydrogenation and pyrolysis effluents.

SUMMARY

We have discovered an improved process for recovering light olefins which utilizes heats of compression to heat reboil streams. These and other features, aspects, and advantages of the present disclosure are further explained by the following detailed description, drawing and appended claims.

DEFINITIONS

Figure 1:
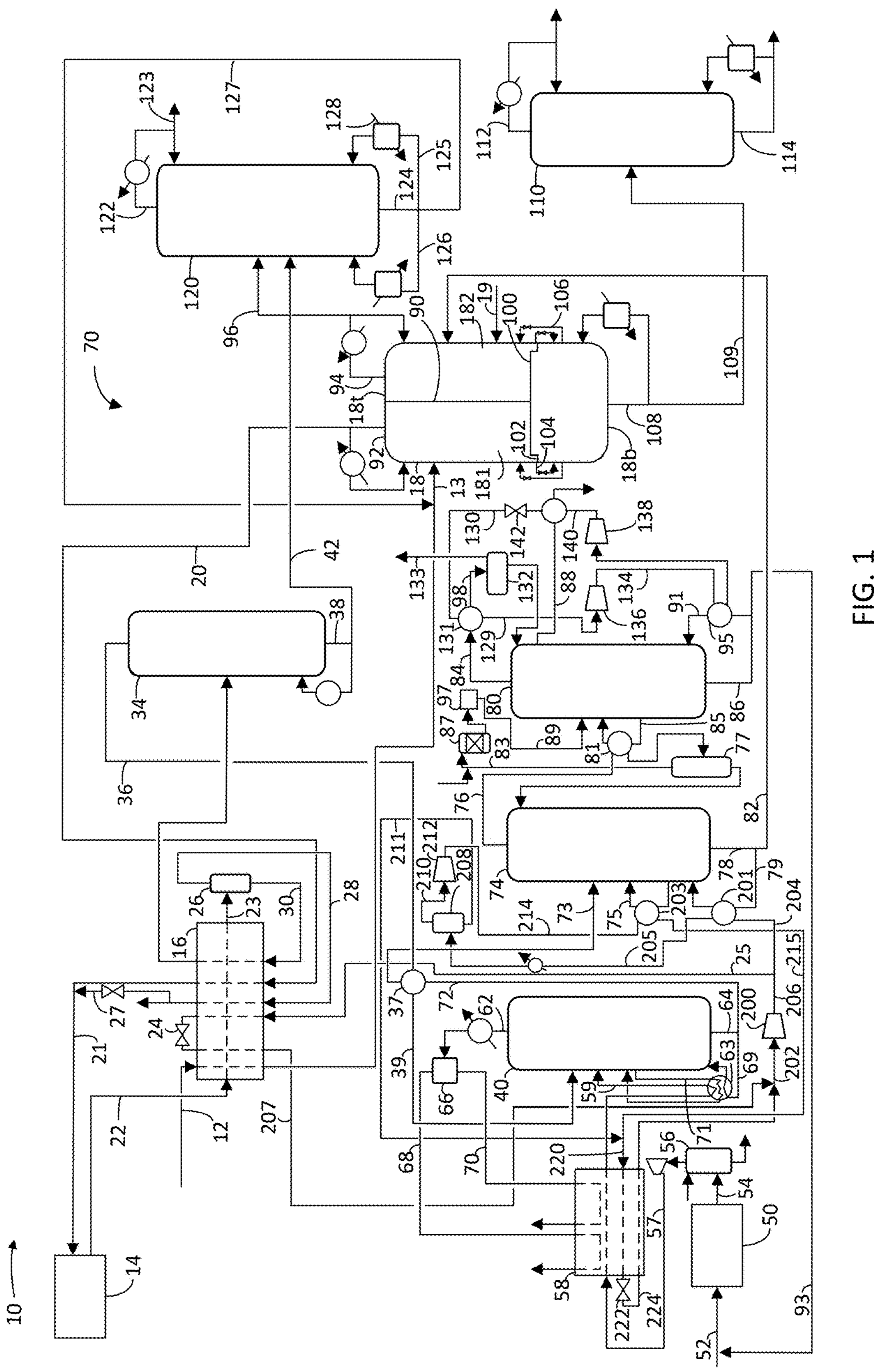
FIG. 1 is a schematic representation of the process and apparatus of the present disclosure.

The following detailed description is merely exemplary in nature and is not intended to limit the application and uses of the embodiment described. Furthermore, there is no intention to be bound by any theory presented in the preceding background or the following detailed description.

The term "communication" means that material flow is operatively permitted between enumerated components.

The term "downstream communication" means that at least a portion of material flowing to the subject in downstream communication may operatively flow from the object with which it communicates.

The term "upstream communication" means that at least a portion of the material flowing from the subject in upstream communication may operatively flow to the object with which it communicates.

The term "direct communication" means that flow from the upstream component enters the downstream component without undergoing a compositional change due to physical fractionation or chemical conversion.

The term "bypass" means that the object is out of downstream communication with a bypassing subject at least to the extent of bypassing.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator that may be operated at higher pressure.

As used herein, the term "predominant" or "predominate" means greater than 50%, suitably greater than 75% and preferably greater than 90%.

The term "$C_X$" is to be understood to refer to molecules having the number of carbon atoms represented by the subscript "x". Similarly, the term "$C_X$−" refers to molecules that contain less than or equal to x and preferably x and less carbon atoms. The term "$C_X$+" refers to molecules with more than or equal to x and preferably x and more carbon atoms.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottom stream back to the bottom of the column. Feeds to the columns may be preheated. The top pressure is the pressure of the overhead vapor at the outlet of the column. The bottom temperature is the liquid bottom outlet temperature. Unless otherwise indicated, overhead lines and bottom lines refer to the net lines from the column downstream of the reflux or reboil to the column. Alternatively, a stripping stream may be used for heat input near the bottom of the column.

As used herein, the term a component "rich stream" or a "stream rich" in a component means that the stream identified as rich coming out of a vessel has a greater concentration of the component than the feed to the vessel.

As used herein, the term a component "lean stream" or a "stream lean" in a component means that the stream identified as lean coming out of a vessel has a lower concentration of the component than the feed to the vessel.

DETAILED DESCRIPTION

The disclosure is a process and apparatus which integrates the recovery of propylene from a paraffin dehydrogenation reactor and a pyrolysis reactor. We have found by utilizing a propane dehydrogenation reactor with a pyrolysis reactor additional production of propylene can accompany abundant ethylene production by pyrolysis. We propose to reboil fractionation streams by heats of compression imparted to compressed refrigerant streams.

The process and apparatus 10 shown in FIG. 1, comprises two conversion units, a paraffin dehydrogenation reactor 14 and a pyrolysis reactor 50 and a common recovery system 70. A propane stream in line 12 is prepared for charge to a propane dehydrogenation reactor 14. The propane stream comprises propane and may comprise other light paraffins such as ethane, normal butane, isobutane, pentane or isopentane. In some embodiments, the propane stream comprises at least one other paraffin having 2 to 30 carbon atoms.

The propane stream in line 12 may be cooled in a PDH cold box 16, or may be bypassed around the cold box, and transported to a depropanizer fractionation column 18, perhaps after supplementation with a propane stream recycled in line 127. In the depropanizer fractionation column 18 propane is separated from heavier components and provided in a first depropanizer overhead stream in line 20. The depropanizer overhead stream in line 20 may be heated or cooled slightly to achieve approximately 35° C. to 40° C. in the dehydrogenation cold box 16 at the outlet and charged to the paraffin dehydrogenation reactor 14 in a dehydrogenation charge line 21.

In the dehydrogenation reactor, propane is dehydrogenated to produce propylene. A dehydrogenation catalyst is used in a dehydrogenation reaction to catalyze the dehydrogenation of propane. The conditions in the dehydrogenation reactor may include a temperature of about 500 to about 800° C., a pressure of about 40 to about 310 kPa and a catalyst to oil ratio of about 5 to about 100.

The dehydrogenation reaction may be conducted in a fluidized manner such that gas, which may comprise the reactant paraffins with or without a fluidizing inert gas, is distributed to the reactor in a way that lifts the dehydrogenation catalyst in the reactor vessel while catalyzing the dehydrogenation of paraffins. During the catalytic dehydrogenation reaction, coke is deposited on the dehydrogenation catalyst leading to reduction of the activity of the catalyst. The dehydrogenation catalyst must then be regenerated in a regenerator. The regenerator may combust coke from the dehydrogenation catalyst and fuel gas to ensure sufficient enthalpy in the dehydrogenation reactor to promote the endothermic reaction.

The dehydrogenation catalyst selected should minimize cracking reactions and favor dehydrogenation reactions. Suitable catalysts for use herein include an active metal which may be dispersed in a porous inorganic carrier material such as silica, alumina, silica alumina, zirconia, or clay. An exemplary embodiment of a catalyst includes alumina or silica-alumina containing gallium, a noble metal, and an alkali or alkaline earth metal.

The catalyst support comprises a carrier material, a binder and an optional filler material to provide physical strength and integrity. The carrier material may include alumina or silica-alumina. Silica sol or alumina sol may be used as the binder. The alumina or silica-alumina generally contains alumina of gamma, theta and/or delta phases. The catalyst support particles may have a nominal diameter of about 20 to about 200 micrometers with the average diameter of about 50 to about 150 micrometers. Preferably, the surface area of the catalyst support is about 85 to about 140 $m^2/g$.

The fluidized dehydrogenation catalyst may comprise a dehydrogenation metal on a support. The dehydrogenation metal may be a one or a combination of transition metals. A noble metal may be a preferred dehydrogenation metal such as platinum or palladium. Gallium is an effective metal for paraffin dehydrogenation. Metals may be deposited on the catalyst support by impregnation or other suitable methods or included in the carrier material or binder during catalyst preparation.

The acid function of the catalyst should be minimized to prevent cracking and favor dehydrogenation. Alkali metals and alkaline earth metals may also be included in the catalyst to attenuate the acidity of the catalyst. Rare earth metals may be included in the catalyst to control the activity of the catalyst. Concentrations of 0.001% to 10 wt % metals may be incorporated into the dehydrogenation catalyst. In the case of noble metals, it is preferred to use about 10 parts per million (ppm) by weight to about 600 ppm by weight noble metal. More preferably it is preferred to use about 10 to about 100 ppm by weight noble metal. The preferred noble metal is platinum. Gallium should be present in the range of 0.3 wt % to about 3 wt %, preferably about 0.5 wt % to about 2 wt %. Alkali and alkaline earth metals may be present in the range of about 0.05 wt % to about 1 wt %.

Regenerated catalyst may be contacted with the propane stream perhaps with a fluidizing gas to lift the propane stream and dehydrogenation catalyst up a riser while dehydrogenation occurs. Above the riser spent dehydrogenation catalyst and propylene product may be separated by a centripetal separation device. Propylene product gas may be quenched with a cooling fluid to prevent over reaction to undesired by-products. Separation of the propylene product may include quench contacting and fractionation to produce a propylene product stream in line 22.

The paraffin dehydrogenation reactor 14 may alternatively employ a catalytic moving bed reactor. The reactor section may comprise several radial flow reactors in parallel or series heated by charge and interstage heaters. The propane stream perhaps with added hydrogen flows in each dehydrogenation reactor from a screened center pipe through an annular dehydrogenation catalyst bed to an outer effluent annulus. Flow may be in the reverse fashion. The dehydrogenation catalyst may comprise a noble metal or mixtures thereof, a modifier selected from the group consisting of alkali metals or alkaline-earth metals and mixtures thereof, a component selected from the group consisting of tin, germanium, lead, indium, gallium, thallium, and mixtures thereof, and a porous support forming a catalyst particle. The catalyst support may comprise oil dropped alumina spheres.

Dehydrogenation conditions may include a temperature of from about 400 to about 900° C., a pressure of from about 0.01 to 10 atmospheres absolute, and a liquid hourly space velocity (LHSV) of from about 0.1 to 100 $hr^{-1}$. The pressure in the dehydrogenation reactor is maintained as low as practicable, consistent with equipment limitations, to maximize chemical equilibrium advantages. Spent dehydrogenation catalyst in the annular catalyst bed may be withdrawn from the bottom of the bed, forwarded to a regenerator to combust coke from the catalyst with air at about 450 to about 600° C. Noble metal on the catalyst may be redispersed by an oxyhalogenation process, dried and returned to the top of the dehydrogenation catalyst bed as regenerated dehydrogenation catalyst.

The dehydrogenated stream in line 22 will comprise light hydrocarbons and hydrogen. The propylene must be separated from other light hydrocarbons such as unreacted propane and hydrogen. Propane can be recycled to the dehydrogenation reactor 14 for propylene production. Hydrogen is a valuable byproduct and may be used elsewhere in the refinery or in the dehydrogenation reactor 14 to control the dehydrogenation reaction.

The dehydrogenated stream in line 22 may be cooled, compressed and dried before hydrogen separation. To separate the hydrogen from the light hydrocarbons effectively, the dehydrogenated stream in line 22 is cryogenically cooled by passing it to a dehydrogenation cold box 16 to condense the hydrocarbons. In the dehydrogenation cold box 16, the dehydrogenated stream in line 22 is cooled by heat exchange with other streams including a dehydrogenation refrigerant stream in line 25 passing through the dehydrogenation cold box 16 to provide a cooled dehydrogenated stream in line 23 which is fed to a dehydrogenation separator 26. The dehydrogenation refrigerant stream in line 25 may have been through a first stage of compression and be at a pressure of about 1400 to about 1700 kPa.

The dehydrogenation refrigerant stream in line 25 may be a mixture of up to 6 components suitably selected to meet the requirements of the propane dehydrogenation unit and pyrolysis unit. The mixed refrigerant composition may comprise about 0 to about 7 mol % inert gas, about 11 to about 35 mol % methane, about 25 to about 40 mol % C2 hydrocarbon, about 20 to about 50 mol % C3 hydrocarbon and about 0 to about 15 mol % C5 hydrocarbon. The inert gas may be nitrogen, and the C5 hydrocarbon may be isopentane. The refrigerant stream in line 25 may pass through the dehydrogenation cold box 16, then expand through an expansion valve 24 to cool the refrigerant stream by the heat of vaporization and pass back through the dehydrogenation cold box 16.

The cooled dehydrogenated stream in line 23 is separated in the dehydrogenation separator 26 to provide a net gas overhead stream rich in hydrogen in a dehydrogenation separator overhead line 28 extending from an overhead of the dehydrogenation separator and a liquid dehydrogenation stream rich in hydrocarbons in a dehydrogenation separator bottoms line 30 extending from a bottom of the separator. The dehydrogenation separator 26 may operate at a temperature between about −100° C. (−150° F.) and about 66° C. (150° F.) and more commonly between about −95° C. (−138° F.) and about −40° C. (−40° F.), and a gauge pressure between about 690 kPa (100 psig) and about 1.4 MPa (200 psig).

The net gas overhead stream in the separator overhead line 28 is sufficiently hydrogen pure from one stage of separation by the thorough condensation of the hydrocarbons in the dehydrogenation separator 26. The net gas overhead stream may possess a hydrogen purity of at least 94 mol %, suitably at least 95 mol %, preferably at least 96 mol % and most preferably at least 96.5 mol % molecular hydrogen. The net gas overhead stream in line 28 can be routed to the dehydrogenation cold box 16 to be heated and provide a product hydrogen stream that can be used elsewhere in the refinery or plant. A hydrogen recycle stream can be taken in a hydrogen recycle line 27 through a control valve thereon from the net gas overhead stream in the separator overhead line 28 to the propane overhead stream in line 20 to provide hydrogen requirements for the dehydrogenation reaction in the dehydrogenation charge line 21. The warmed off-gas stream may be provided at a temperature of about 32° C. (90° F.) to about 60° C. (140° F.) and a gauge pressure of about 760 kPa (110 psig) to about 1.2 MPa (170 psig).

The liquid dehydrogenation stream in the dehydrogenation separator bottoms line 30 is rich in hydrocarbons that can be refined for valuable products. The liquid dehydrogenation stream in the dehydrogenation separator bottoms line 30 may be heated by passing it through the dehydrogenation cold box 16 to vaporize the hydrocarbons. The vaporized hydrocarbons in line 30 are heated by giving up the heat of vaporization and therefore assist in cooling the dehydrogenated stream passed through the dehydrogenation cold box 16 in line 22. The requisite heat exchange in the dehydrogenation cold box 16 occurs between the cold and the hot streams and the dehydrogenation refrigerant stream in line 25. The liquid dehydrogenated stream in line 30 is heated by passing it through the dehydrogenation cold box 16 and fed to the dehydrogenation stripping column 34.

The liquid dehydrogenation stream in line 30 comprises some light ends like methane and ethane that must be separated from larger hydrocarbons like propylene and propane. Hence, the liquid dehydrogenation stream in line 30, after heating in the dehydrogenation cold box 16 to a temperature of about 0° C. (30° F.) to about 45° C. (113° F.) is passed to a dehydrogenation stripping column 34 for fractionation. The dehydrogenated stripping column 34 separates the liquid dehydrogenated stream into a stripping overhead stream rich in C2− hydrocarbons along with some slipped C3 hydrocarbons in a stripping overhead line 36 extending from an overhead of the stripping column which is rich in methane and ethane and a stripping bottoms stream in a stripping bottoms line 38 extending from a bottom of the stripping column 34 which is rich in C3 hydrocarbons. The stripping removes light ends with a limited quantity of C3 hydrocarbons in the overhead vapor. However, the C3 hydrocarbons are recovered in a demethanizer column 40 to which the stripping overhead stream is routed. The stripping overhead stream in line 36 is heat exchanged with a demethanizer bottoms stream in line 72 to cool the stripping overhead stream in a heat exchanger 37 and fed as a demethanizer feed stream in a demethanizer feed line 39 to the demethanizer column 40 to remove methane and lighter gases from the stripping overhead stream. The stripping bottoms stream in the stripping bottoms line 38 is split into a reboil stream which is reboiled and returned to the paraffin dehydrogenation stripping column 34 and a net stripping bottoms stream is transported in a net stripping bottoms line 42 to a C3 splitter column 120. The stripping column 34 may operate at a bottoms temperature of about 30° C. (90° F.) to about 60° C. (140° F.) and an overhead gauge pressure of no more than about 1.5 to about 1.9 MPa (gauge). The stripping column 34 may be in downstream communication with paraffin dehydrogenation reactor 14.

The process and apparatus 10 omit a paraffin dehydrogenation deethanizer column and cryogenic cooling equipment associated therewith necessary for propylene recovery. Instead, propylene recovery will take place downstream of the pyrolysis reactor 50.

A refrigerant stream in a preliminary refrigerant line 202 is fed to a first refrigerant compressor 200 in which it is compressed to a pressure of about 1500 kPa to about 1750 kPa in a first stage of compression to provide a first compressed refrigerant stream in line 206. The refrigerant stream may be a mixed refrigerant stream as previously described. The first compressed refrigerant stream in line 206 is split into a reboil refrigerant stream in line 204 and the dehydrogenation refrigerant stream in line 25. The reboil refrigerant stream in line 204 is heat exchanged on a first side of a deethanizer bottom reboil exchanger 201 with a deethanizer bottom reboil stream on a second side of the deethanizer bottom reboil exchanger in a reboil line 79 taken from the deethanizer bottom stream in line 78 to boil up the deethanizer bottom reboil stream and cool the first compressed refrigerant stream in line 204 to provide a cooled first compressed refrigerant stream in line 205 and a boiling deethanizer bottom reboil stream which is returned to the deethanizer column. The cooled first compressed refrigerant stream in line 205 is further cooled to near ambient temperature in a cooler and is separated in a separator 208 to provide a second compression refrigerant stream in an overhead line 210 and remove liquid in a second compression liquid stream in a bottoms line 211. If necessary, supplemental bottom reboiling in the deethanizer column 74 may be necessary and provided by a low-level heat stream, apart from the heat provided by the first compressed refrigerant stream in line 204.

The dehydrogenation refrigerant stream is taken in line 25 from the cooled first compressed refrigerant stream in line 206 and is transported to the dehydrogenation cold box 16 in which it is heat exchanged with a dehydrogenated stream in line 22 to cool the dehydrogenated stream and other streams resulting in heating the dehydrogenation refrigerant stream in line 207. After passing through the dehydrogenation cold box 16, the cooled dehydrogenation refrigerant stream in line 25 is passed through an expansion valve 24 to vaporize the dehydrogenation refrigerant stream thereby cooling it and providing a vaporized dehydrogenation refrigerant stream in line 207. The vaporized dehydrogenation refrigerant stream in line 207 passes back through the dehydrogenation cold box 16 to further provide net cooling to the streams passing therethrough including the dehydrogenated stream in line 22. A warmed vaporized dehydrogenation refrigerant stream in line 207 is returned to provide a portion of the refrigerant stream in the preliminary refrigerant line 202.

The second compression refrigerant stream in line 210 from the overhead of the separator 208 is compressed in a second compressor 212 to a pressure of about 4500 to about 5500 kPa in a second stage of compression to provide a second compressed refrigerant stream in line 214. The second compressed refrigerant stream in line 214 is heat exchanged on a first side of a deethanizer side reboil exchanger 203 with a deethanizer side reboil stream in line 75 from the deethanizer column 74 on a second side of the deethanizer side reboil exchanger to reboil the side reboil stream and cool the second compressed refrigerant stream in line 214 to provide a cooled second compressed refrigerant stream in line 215. The second compressed refrigerant stream in line 214 can also undergo further cooling in an additional exchanger if needed. The cooled second compressed refrigerant stream in line 215 may be joined with the second compression liquid stream in line 211 from the separator 208 to provide a total second compressed refrigerant stream in line 220 to the pyrolysis cold box 58. The deethanizer side reboil exchanger 203 may be in downstream communication with said second compressor on a refrigerant first side of the compressor.

The total second compressed refrigerant stream in line 220 is then passed to a pyrolysis cold box 58 in which it is heat exchanged with a treated pyrolyzed stream in line 57 to heat the treated pyrolyzed stream and other streams and cool the total second compressed refrigerant stream in line 220. After passing through the pyrolysis cold box 58, the total second compressed refrigerant stream in line 220 is passed through an expansion valve 222 to vaporize the total second compressed refrigerant stream thereby cooling it further and providing a vaporized second compressed refrigerant stream in line 224. The vaporized second compressed refrigerant stream in line 224 may be passed back through the pyrolysis cold box 58 to provide net cooling to the streams passing therethrough including the treated pyrolyzed stream in line 57. A warmed vaporized dehydrogenation refrigerant stream in line 224 is returned to provide a portion of the refrigerant stream in the preliminary refrigerant line 202.

A pyrolysis charge stream in charge line 52 perhaps supplemented with recycle ethane from line 93 is charged to a pyrolysis reactor 50 which may be a steam cracking furnace for cracking of hydrocarbons under steam to produce a pyrolyzed stream in pyrolysis line 54. The cracking feed stream may optionally be in the gas phase. The pyrolysis reactor 50 may preferably, be operated at a temperature of about 750° C. (1382° F.) to about 950° C. (1742° F.). The pyrolysis charge stream may be one of many feed streams that enter at the same point of the furnace, or at separate points to maximize product yields. The pyrolysis charge stream may be an ethane stream or a naphtha stream.

The pyrolyzed stream exiting the pyrolysis reactor 50 in pyrolysis line 54 may be in a superheated state. One or more quench columns, or other devices not shown, but preferably an oil quench column and/or a water quench column, may be used for quenching the pyrolyzed stream. The pyrolyzed stream may be caustic washed in a scrubber column 56 to remove acid gases and the scrubbed gas compressed to provide a treated pyrolyzed stream in line 57 before it is cooled in a pyrolysis cold box 58.

Although other streams may be recovered from the pyrolysis reactor 50, the treated pyrolyzed stream in line 57 is a gaseous hydrocarbon stream. The treated pyrolyzed stream in line 57 is cooled in the pyrolysis cold box 58 by heat exchange with the net gas from the demethanizer column 40 in lines 68 and 70 and the vaporized second compressed refrigerant stream in line 224 after being expanded across valve 222 and fed to the demethanizer column 40. The demethanizer column 40 may be in downstream communication with the paraffin dehydrogenation reactor 14, the pyrolysis reactor 50 and the stripping column 34.

In the demethanizer fractionation column the cooled stripping overhead stream in line 39 rich in C2− hydrocarbons along with some slipped C3 hydrocarbons and the cooled pyrolyzed stream in a demethanizer feed line 59 are fractionated together to provide a demethanizer overhead stream rich in methane and hydrogen in the demethanizer overhead line 62 and a demethanized bottoms stream in a demethanizer bottoms line 64 which is rich in C2+ hydrocarbons. The cooled treated pyrolyzed stream in the in line 57 may be cooled in a demethanizer reboiler heat exchanger 63 by heat exchange with a bottom reboil stream in line 69 to cool the cooled treated pyrolyzed stream in line 57 to provide a demethanizer feed stream in line 59 and a reboiled bottom stream in line 69 that is returned boiling to the column. The cooled treated pyrolyzed stream in the in line 57 may also be cooled in the demethanizer reboiler heat exchanger 63 by heat exchange with a side reboil stream in line 71 to further cool the cooled pyrolyzed stream in line 57 to provide the demethanizer feed stream in line 59 and a reboiled side stream in line 71 that is returned boiling to the column. The demethanizer feed stream in line 59 may be additionally cooled by expanding across a turboexpander that is not shown in FIG. 1. The demethanized overhead stream with very minimal ethylene loss is achieved by providing a cooled reflux by utilizing a side stream from a suitable tray near a top of the demethanizer column 40, comprising very little ethylene. The sides stream is compressed, cooled and returned to the demethanizer column 40 as reflux. Allowing slippage of a predominantly C1− stream of hydrogen and methane as a net overhead streams of the demethanizer column 40 also minimizes ethylene loss. The arrangement of the reflux stream is not shown in FIG. 1. The hydrogen and methane are further separated by further chilling in a demethanizer cooler and separated in a hydrogen-methane separator 66 to provide a net gas stream in the net overhead line 68 rich in hydrogen and a net liquid stream rich in methane in a net liquid line 70 which are both sent to the pyrolysis cold box 58 to provide cooling to the treated pyrolyzed stream in line 57.

The demethanized bottoms stream in line 64 is split into a bottom reboil stream in the bottom reboil line 69 which is reboiled by heat exchange in the demethanizer reboil exchanger 63 with the treated pyrolyzed stream in line 57 and returned to the demethanizer column 40 and a net demethanized bottom stream in a net demethanizer bottoms line 72 which is heat exchanged in the heat exchanger 37 with the stripping overhead stream in line 36 to warm the net demethanized stream in line 72 to provide a warmed net deethanized stream in a deethanizer feed line 73 before the net demethanized stream is fed to a deethanizer column 74 and cool the stripping overhead stream in line 36.

The deethanizer column 74 fractionates the net demethanizer bottoms stream in the deethanizer feed line 73 into a deethanizer overhead stream in line 76 rich in C2 hydrocarbons and a deethanized bottoms stream in line 78 rich in C3+ hydrocarbons. The deethanizer overhead stream in line 76 is condensed in an C2 splitter side reboiler 81 with a C2 splitter side stream in line 85 taken from a side of the C2 splitter column 80. The condensed overhead stream in line 76 is fed to a deethanizer receiver 77 in which it is separated into a liquid reflux stream that is refluxed back to the deethanizer column 74 and a net deethanizer overhead stream in line 83 fed to an C2 splitter column 80.

The net deethanizer overhead stream in line 83 may comprise acetylenes that require selective hydrogenation to make it a suitable ethylene feed for a polymerization plant. The deethanizer overhead stream may be at an appropriate pressure for selective hydrogenation. The net deethanizer overhead stream in line 83 may mixed with a hydrogen stream and be treated in an acetylene selective hydrogenation reactor 87 to convert acetylene to ethylene and dried to provide a selectively hydrogenated deethanizer overhead stream in line 89.

In the selective hydrogenation reactor 87, selective hydrogenation of C2− multi-olefins occurs. A broad range of suitable operating pressures in the selective hydrogenation reactor 87 range from about 276 kPag (40 psig) to about 5516 kPag (800 psig), or about 345 kPag (50 psig) to about 2069 kPag (300 psig). A relatively moderate temperature between about 25° C. (77° F.) and about 350° C. (662° F.), or about 50° C. (122° F.) to about 200° C. (392° F.) is typically employed. The vapor hourly space velocity of the reactants for the selective hydrogenation catalyst may be about 30 hr-1, or above about 300 hr-1, or above about 15 hr-1, to about 600 hr-1. To avoid the undesired saturation of a significant amount mono-olefinic hydrocarbons, the mole ratio of hydrogen to multi-olefinic hydrocarbons in the material entering the bed of selective hydrogenation catalyst is maintained between 0.75:1 and 1.8:1.

A selective hydrogenation catalyst may be any suitable catalyst which is capable of selectively hydrogenating acetylene in a C2-hydrocarbon stream. A particularly preferred selective hydrogenation catalyst comprises copper and at least one other metal such as titanium, vanadium, chrome, manganese, cobalt, nickel, zinc, molybdenum, and cadmium or mixtures thereof. The metals are preferably supported on inorganic oxide supports such as silica and alumina. Preferably, a selective hydrogenation catalyst may comprise a copper and a nickel metal supported on alumina. The selective hydrogenated effluent may exit the selective hydrogenation reactor 87 and enter a drier 97. The drier 97 provides a dried gaseous stream in a the selectively hydrogenated deethanizer overhead line 89 and may be fed to the C2 splitter column 80.

The deethanized bottom stream in line 78 provides a bottom reboil stream in line 79 which is reboiled by heat exchange in a deethanizer bottoms reboil exchanger 201 with the first compressed refrigerant stream in line 204 and fed back to the deethanizer column 74. The deethanized bottom stream in line 78 also provides a net deethanized bottom stream that is fed to the depropanizer column 18 in line 82. The deethanizer column 74 operates at an overhead temperature of about −10° C. (15° F.) to about −32° C. (−25° F.) and a bottoms gauge pressure of about 1.1 MPa (160 psig) to about 2.4 MPa (350 psig). The deethanizer bottoms reboil exchanger 201 may be in downstream communication with a first compressor on a refrigerant first side of the deethanizer bottoms reboil exchanger 201.

The selectively hydrogenated deethanizer overhead stream in a C2 splitter feed line 89 is rich in C2 hydrocarbons and is fed to a C2 splitter column 80. The C2 splitter column 80 fractionates the deethanizer overhead stream in line 89 into a C2 splitter overhead stream rich in ethylene in a C2 splitter overhead line 84 and a C2 splitter bottoms stream rich in ethane in a C2 splitter bottoms line 86. The C2 splitter overhead stream in line 84 is condensed by heat exchange in a C2 splitter condenser 131 with an expanded cooled second compressed propylene refrigerant stream in line 130 to provide a condensed C2 splitter overhead stream in line 98 and a propylene refrigerant stream in line 129. The condensed C2 splitter overhead stream in line 98 is separated in a C2 splitter receiver 132 into a liquid stream that is refluxed to the C2 splitter column 80 and a small quantity of net vapor C2 splitter overhead stream of off gases in a net C2 splitter overhead line 133 which may be separated in the demethanizer column 40. A side liquid stream may be taken as a product ethylene stream from a side near the top of the C2 splitter column in line 88 at an elevation below the reflux feed to the column. The C2 splitter bottom stream in line 86 provides a reboil C2 splitter bottom stream in line 91. The reboil C2 splitter bottom stream is reboiled by heat exchange in a C2 splitter bottoms reboiler 95 with a first propylene refrigerant compressed stream in line 134 from a first propylene refrigerant compressor 136 to provide a reboiled C2 splitter bottom stream that is fed back to the C2 splitter column 80 and a cooled first compressed propylene refrigerant stream. The first propylene refrigerant compressor 136 may be preceded by a knock-out drum to remove liquid before compression.

The C2 splitter bottom stream in line 86 provides a net C2 splitter bottom stream rich in ethane that is recycled in line 93 and charged to the pyrolysis reactor 50 perhaps via line 52 to produce more ethylene. The ethane recycle stream in line 93 may be heat exchanged with the treated pyrolyzed stream 57 to cool the pyrolyzed stream in the pyrolysis cold box 58. In this way the ethane recycle stream 93 may be heated before it is fed to pyrolysis reactor 50 which is not shown in FIG. 1. The C2 splitter column 80 operates at an overhead temperature of about −32° C. (−25° F.) to about −60° C. (−75° F.) and a bottoms gauge pressure of about 690 kPag (100 psig) to about 1.8 MPa (260 psig). The C2 splitter column 80 can alternatively use a heat pump compression scheme in which the operating temperature and pressure of the C2 Splitter column 80 can be much lower such as about 0.55 MPag (80 psig) to about 1 MPag (150 psig) and an overhead temperature of about −65° C. (−85° F.) to about −40° C. (−40° F.).

The cooled first propylene refrigerant stream in line 134 that is cooled from boiling up the C2 splitter bottoms stream is compressed in a second propylene refrigerant compressor 138 to provide a second compressed propylene refrigerant stream. The second propylene refrigerant compressor 138 may be preceded by a knock-out drum to remove liquid before compression. The second compressed propylene refrigerant stream in line 140 may be heat exchanged with the ethylene product stream in line 88 to heat and vaporize the ethylene which may be taken from the column as a liquid stream to provide a heated ethylene product stream and a cooled second compressed propylene refrigerant stream. The cooled and liquified second propylene refrigerant compressor stream may be expanded in a throttling valve 142 to further cool the propylene refrigerant stream in line 130 to provide refrigerant to the C2 splitter condenser 131.

The depropanizer column 18 may be in downstream communication with the pyrolysis reactor 50. The depropanizer column 18 may receive at least two C3 feeds. The first C3 feed stream is the dehydrogenation charge stream in line 12 supplemented with a propane recycle stream in a net C3 splitter bottoms line 127 in a first depropanizer feed line 13. The second C3 feed stream is the net deethanized bottom stream fed to the depropanizer column 18 in the net deethanizer bottoms line 82. The dehydrogenation charge stream in line 12 may be fed to the depropanizer column 18 after passing through the dehydrogenation cold box 16 or fed directly, bypassing the dehydrogenation cold box. The first C3 feed stream in line 12 and the second C3 feed stream in line 82 are fractionated in the same depropanizer column 18.

The first C3 feed is rich in propane. The second C3 feed will typically be rich in propylene and more heavy hydrocarbons because it contains the pyrolysis effluent. Therefore, the first C3 feed stream comprising propane in line 12 may be supplemented with a recycle propane stream from the C3 splitter column 120 in a net C3 splitter bottoms line 127 to provide a first depropanizer feed stream in a depropanizer line 13 and fed to a first side 181 of the depropanizer column 18. The second C3 feed stream comprising a deethanized pyrolyzed stream in the net deethanizer bottom line 82 is fed to a second side 182 of the depropanizer column 18. The depropanizer column 18 comprises a dividing wall 90 and the first depropanizer feed stream in the first depropanizer feed line 13 is fed to a first side 181, and the second depropanizer feed stream in the net deethanizer bottom line 82 is fed to the second side 182 of a dividing wall 90 of the same depropanizer column 18. The dividing wall may be vertical and divide the top **18*t* of the depropanizer column 18 into the first side 181 and the second side 182 and impedes horizontal flow of the two feeds thus preventing cross-contamination between the two feeds. The dividing wall 90 extends to the top 18*t* of the depropanizer column 18 but is spaced apart from the bottom 18*b* of the depropanizer column. The depropanizer column 18 fractionates the first C3 feed stream in line 13 into a propane charge stream and a C4+ hydrocarbon stream and the second C3 stream in line 82 into a C3 pyrolyzed stream and the C4+ hydrocarbon stream. A C3 stream in line 19 from another source, such as from a condensate stripping column may be fed to the second side 182 of the depropanizer column 18**.

A first depropanizer overhead stream is taken from the top **18*t* of the first side 181 of the depropanizer column in line 92, is condensed and a portion refluxed to the first side 181 of the column as reflux while a net first depropanizer overhead stream in line 20 is taken as the propane charge stream to the paraffin dehydrogenation reactor 14. The paraffin dehydrogenation reactor 14 may be in downstream communication with the depropanizer column 18 and specifically the first side 181 of the depropanizer column. A second depropanizer overhead stream is taken from the top 18*t* of the second side 182 of the depropanizer column in line 94, is condensed and a portion refluxed to the second side of the column as reflux while a net second depropanizer overhead stream is taken as a C3 pyrolyzed stream in line 96 for feed to a C3 splitter column 120. The C3 splitter column 120 may be in downstream communication with the depropanizer column 18 and specifically the second side 182 of the depropanizer column 18. The C3 splitter column 120 may also be in downstream communication with dehydrogenation reactor 14 and the pyrolysis reactor 58. The dehydrogenation reactor 14 may also be in downstream communication with the C3 splitter column 120. The overhead streams in lines 20 and 96 may be taken at a temperature of about 35 to about 65° C. and a pressure of about 1.5 to about 1.9 MPa (g) which are the conditions in the overhead of the depropanizer column 18**.

The depropanizer column 18 may also include an internal wall 100 which may be horizontal for separating the top **18*t* from the bottom 18*b* of the column. The internal wall 100 may be located below the dividing wall 90. The bottom edge of the dividing wall 90 may be sealed to the top of the internal wall 100 to further minimize cross mixing of components of the two C3 feeds. The internal wall 100 impedes vertical flow in the column but need not be a pressure retaining wall. A perimeter well 102 collects liquid from above the internal wall 100 which is transported to below the wall by routing the liquid from above the internal wall perhaps out of the column 18 and back in below the internal wall through valved liquid pipes 104. Vapor from below the internal wall 100 may be transported through vapor pipes 106 with control valves thereon for controlling the vapor flow rate to above the internal wall. About 25 to about 40% of the trays in the depropanizer column may be below the internal wall 100. The control valves on the vapor pipes 106 permit controlling vapor flow rates from below the internal wall 100 to above the internal wall on the first side 181 and controlling vapor flow rates from below the internal wall 100 to above the internal wall on the second side 182 of the dividing wall. The vapor pipes 106 are shown transporting vapor out of the column 18**, but transport may be within the column.

Below the internal wall 100, a single C4+ stream is produced in a depropanized bottoms line 108. A reboil up stream is taken from the bottoms line 108, boiled up and returned to the column. A net depropanized bottoms stream is taken in line 109 below the internal wall 100 and may be fed to a debutanizer column 110. The bottoms temperature of the column may be between about 70 and about 130° C.

The depropanized bottoms stream in line 109 rich in C4+ hydrocarbons may be fractionated in a debutanizer column 110 to provide an overhead stream comprising butanes in line 112 and a bottoms stream comprising a pyrolysis oil stream comprising C5+ hydrocarbons in a bottoms line 114. The debutanizer column 110 may be in downstream communication with a bottoms line 108 of the depropanizer column 18. The debutanizer overhead stream is withdrawn from the debutanizer column 110 in a debutanizer overhead line 112. The debutanizer overhead stream in line 112 comprising mixed butanes may be recovered to be further sent for butadiene extraction (not shown) in a petrochemical facility or valorized in other ways by further processing.

The debutanizer bottoms stream withdrawn in line 114 from the bottom of the debutanizer column 110 is a pyrolysis oil rich in C5+ hydrocarbons may be suitable for downstream processing in a hydrotreating unit. The debutanizer column 110 operates in a bottoms temperature range of about 140° C. (284° F.) to about 190° C. (374° F.), preferably about 140° C. (284° F.) to about 170° C. (338° F.) and an overhead pressure range of about 450 kPag (65 psig) to about 700 kPag (100 psig).

The C3 splitter column 120 fractionates the C3 pyrolyzed stream from the second side 182 of the depropanizer column 18 in the C3 pyrolyzed stream in line 96 and the net stripped dehydrogenation stream in line 42 into a propylene product stream in a C3 splitter overhead line 122 and a propane recycle stream in a C3 splitter bottoms line 124.

In a first embodiment, the C3 pyrolyzed stream in line 96 and the net stripped dehydrogenation stream in line 42 are fed to the same C3 splitter fractionation column 120. The C3 pyrolyzed stream in line 96 is fed to the C3 splitter fractionation column 120 at an elevation above the feed of the net stripped dehydrogenation stream in line 42 to the C3 splitter fractionation column. A propylene overhead stream is taken from an overhead of the C3 splitter column in an overhead line 122 extending from an overhead of the column, is condensed and a portion refluxed to the column as reflux while a net propylene product stream in line 123 is taken as a propylene product stream. In this embodiment, the overhead pressure is between about 1.5 and about 1.9 MPa (gauge). The condenser may be cooled by cooling water. The propane recycle stream may be taken in a C3 splitter bottoms line 124 rich in propane and be split into three streams. A first stream is a first bottoms reboil stream in line 125 which may be boiled up by heat exchange with low pressure stream. A second stream is a second bottoms reboil stream in line 126 which may be boiled up by heat exchange with quench water stream in a quench water line 128, which is a waste heat stream available from circulating hot water in the pyrolysis unit and used for quenching the pyrolysis reactor effluent and/or other warm streams. The second reboil stream in line 126 may be boiled up by the entire pyrolysis quench water stream in line 128. The quench water stream in line 128 may provide sufficient or nearly sufficient heating requirements for the C3 splitter column 120. The remaining heat duty may be provided by low pressure steam or by a heat pump compressor.

The third stream taken from the bottoms stream 124 is the net propane recycle stream in line 127 which may be recycled to the first side 181 of the depropanizer column 18 to remove C4+ hydrocarbons from propane charge stream in line 12 which after fractionation is charged to the paraffin dehydrogenation reactor 14 for dehydrogenation in the first depropanizer overhead stream in line 20. The propylene recovery from the propane-propylene splitter column 120 can be at least 99 wt % of at least 99.5 wt % purity.

Figure 2:
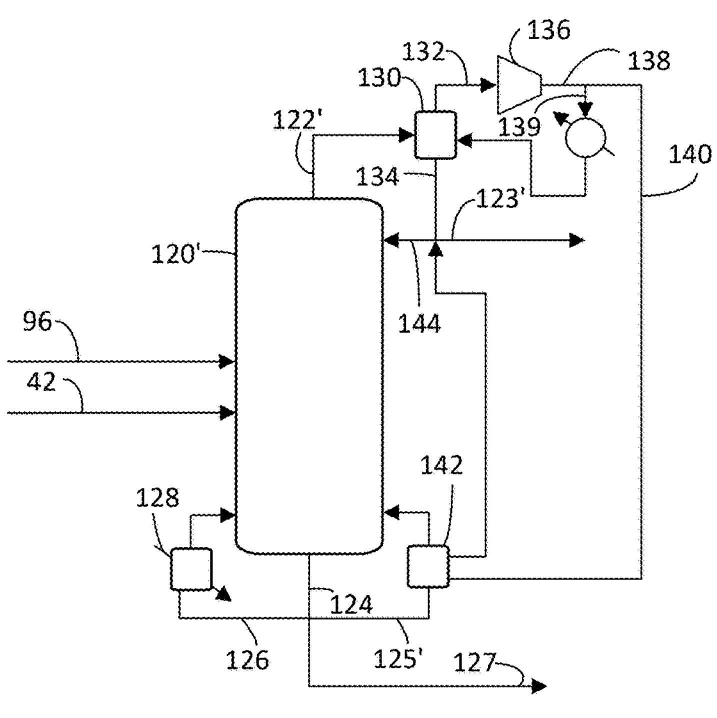
FIG. 2 is a schematic representation of an alternative embodiment of the process and apparatus of FIG. 1.

FIG. 2 shows an alternative embodiment of a C3 splitter column 120' that utilizes a heat pump compressor but operates at a lower pressure. Elements in FIG. 2 with the same configuration as in FIG. 1 will have the same reference numeral as in FIG. 1. Elements in FIG. 2 which have a different configuration as the corresponding element in FIG. 1 will have the same reference numeral but designated with a prime symbol ('). The configuration and operation of the embodiment of FIG. 2 is essentially the same as in FIG. 1.

A propylene overhead stream is taken in line 122' and fed to a compressor drum 130. In the compressor drum 130, a vapor overhead stream in a drum overhead line 132 extending from an overhead of the drum is separated from an overhead liquid stream in a drum bottoms line 134 extending from a bottom of the drum. The overhead vapor stream in the drum overhead line 132 is compressed in a compressor 136 to provide a compressed vapor stream in line 138. A return portion of the compressed vapor stream is cooled, condensed, perhaps by process heating, and returned to the compressor drum 130 in line 139 while a reboil portion in line 140 is heat exchanged with a first boil up stream in a first reboil line 125' in a first reboiler 142 and refluxed to the column in line 144. A propylene product stream may be taken in line 123'.

The overhead pressure in the C3 splitter column 120' is between about 650 kPa to about 1.3 MPa (g). The bottoms temperature may be between about 20° C. and about 60° C.

Figure 3:
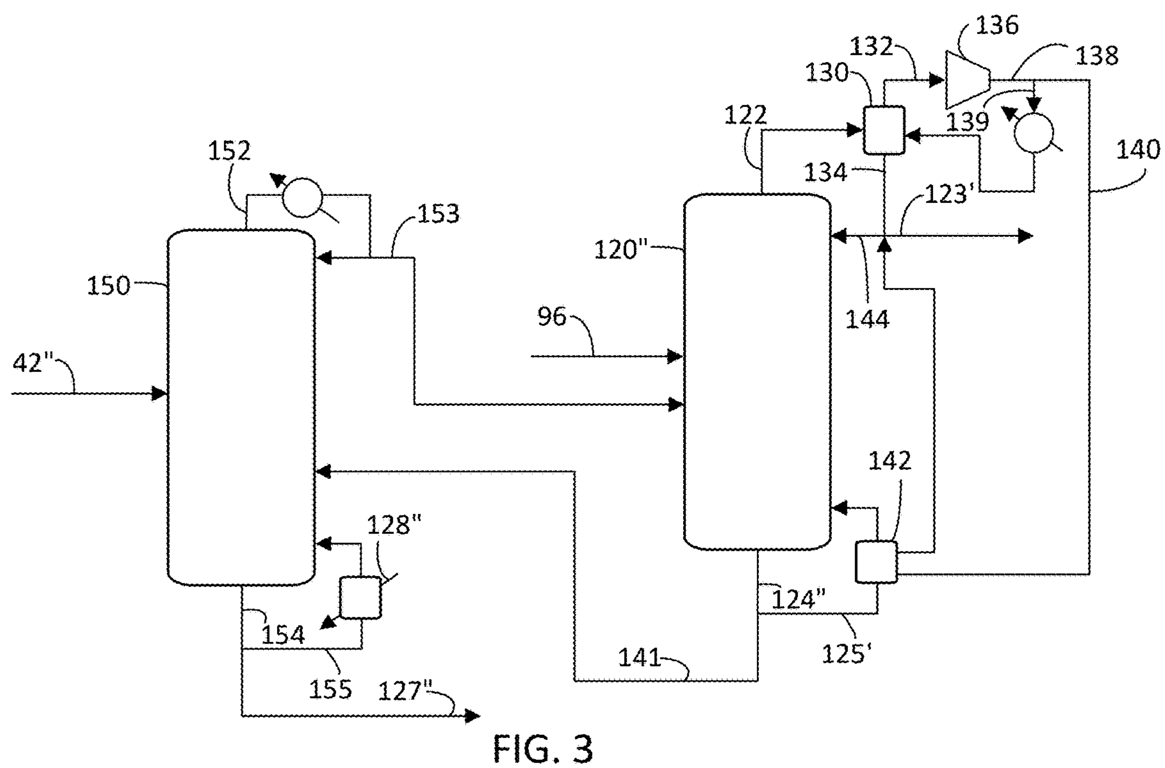
FIG. 3 is a schematic representation of an alternative embodiment of the process and apparatus of FIG. 2.

FIG. 3 shows an alternative embodiment of a C3 splitter column 120" that utilizes a prefractionation C3 splitter column 150 in addition to a main C3 splitter fractionation column 120". Elements in FIG. 3 with the same configuration as in FIG. 2 will have the same reference numeral as in FIG. 2. Elements in FIG. 3 which have a different configuration as the corresponding element in FIG. 2 will have the same reference numeral but designated with a double prime symbol ("). The configuration and operation of the embodiment of FIG. 3 is essentially the same as in FIG. 2.

The net stripped dehydrogenation stream in the stripping bottoms line 42" is prefractionated first in the prefractionation C3 splitter column 150 to provide a prefractionation stream rich in propylene in a prefractionation overhead line 152 and a prefractionation bottoms stream 154 rich in propane. The prefractionation column 150 may be in downstream communication with the dehydrogenation reactor 14. The prefractionation stream in the overhead line 152 is condensed and a portion refluxed to the column as reflux while a net prefractionation stream rich in propylene in a net overhead line 153 is fed to the main C3 splitter column 120". The purity of the propylene rich stream in line 153 is maximized by using the waste heat stream available in a quench water stream to boil up the reboil stream in line 155 for the prefractionator C3 splitter column 150. In this embodiment, the overhead pressure in the prefractionation C3 splitter column 150 is between about 1.5 and about 1.9 MPa (gauge). The condenser may be cooled by cooling water. A prefractionation bottoms stream may be taken in line 154 rich in propane and be split into two streams. A first stream is a first bottoms reboil stream in line 155 which may be boiled up by heat exchange with quench water stream and/or other warm stream in line 128". The second stream taken from the prefractionation bottoms stream 154 is a net propane recycle stream in line 127" which may be recycled to the propane charge stream in line 12 which is charged to the paraffin dehydrogenation reactor 14 for dehydrogenation after fractionation on the first side 181 of the depropanizer column 18 to remove C4+ hydrocarbons. The net propane recycle stream in line 127" may have no more than about 1 mol % propylene. The bottoms temperature of the prefractionation column may be between about 50° C. and about 60° C.

The prefractionation stream in line 153 rich in propylene and the C3 pyrolyzed stream in the net second depropanizer overhead line 96 are both fractionated in the main C3 splitter column 120". The main C3 splitter column 120" may be in downstream communication with the prefractionation column 150. The C3 pyrolyzed stream in the net second depropanizer overhead line 96 may be fed to the main C3 splitter column 120" at a higher elevation than the feed of the prefractionation stream in line 153. A propylene overhead stream is taken in line 122 and fed to a compressor drum 130. In the compressor drum 130, a vapor overhead stream in a drum overhead line 132 extending from an overhead of the drum is separated from an overhead liquid stream in a drum bottoms line 134 extending from a bottom of the drum. The overhead vapor stream in the drum overhead line 132 is compressed in a compressor 136 to provide a compressed vapor stream in line 138. A return stream of the compressed vapor stream is cooled and returned to the compressor drum 130 in line 139 while a reboiling stream in line 140 is heat exchanged with a C3 splitter bottoms reboil stream in a reboil line 125' in a reboiler exchanger 142 and refluxed to the column in line 144. A propylene product stream is taken in line 123'. The main C3 splitter column 120" performs the residual purification of the propylene product stream that is required after maximizing the purification in the prefractionator C3 splitter column 150 utilizing waste heat in the quench water stream to reboil the boil up stream in line 155.

A main bottoms stream in line 124" is taken from a bottom of the main C3 splitter column 120" and is split into two streams. A first stream is a bottoms reboil stream in the reboil line 125' which may be boiled up by heat exchange with the reboiling stream of the of the compressed vapor stream in line 140. The second stream is a net main C3 splitter bottom stream in line 141 which may have no more than 2 mol % propylene or even less depending on the extent of purification achieved in the prefractionator C3 splitter column 150. The net main C3 splitter stream may be recycled to the prefractionation C3 splitter column 150 to be prefractionated with the net stripped dehydrogenation stream in the net stripping bottoms line 42". The net main C3 stream in line 141 may be fed to the prefractionation column 150 at a lower elevation than the net stripped dehydrogenation stream in the net stripping bottoms line 42".

The overhead pressure in the main C3 splitter column 120" may be between about 650 kPa (g) to about 1.3 MPa (g). The bottoms temperature may be between about 20° C. and about 60° C.

Figure 4:
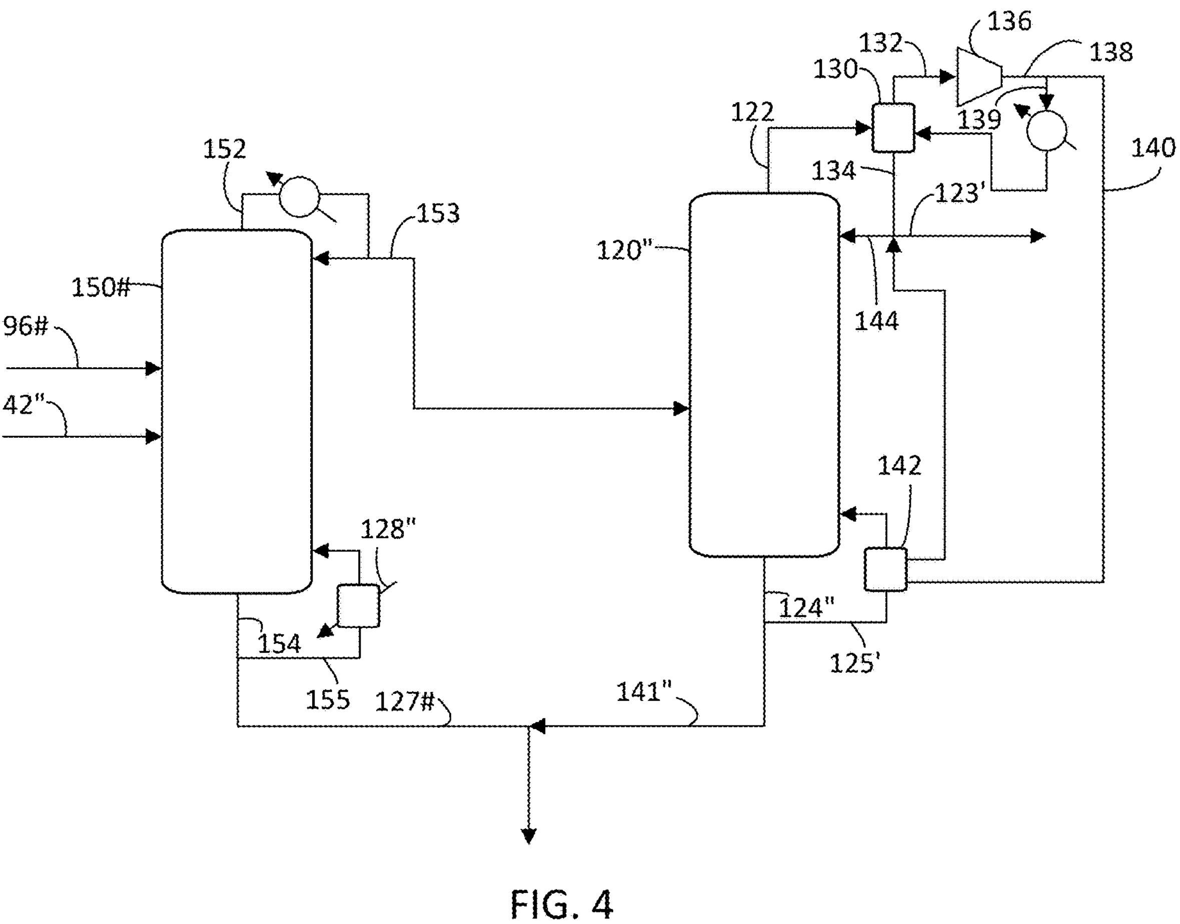
FIG. 4 is a schematic representation of an alternative embodiment of the process and apparatus of FIG. 3.

FIG. 4 shows an alternative embodiment of a C3 splitter column 120" that utilizes a prefractionation C3 splitter column 150 # in addition to the main C3 splitter fractionation column except both the C3 pyrolyzed stream in the net second depropanizer overhead line 96 # and the net stripped dehydrogenation stream in the stripping bottoms line 42" are prefractionated in the prefractionation C3 splitter column 150 # together. Elements in FIG. 4 with the same configuration as in FIG. 3 will have the same reference numeral as in FIG. 3. Elements in FIG. 4 which have a different configuration as the corresponding element in FIG. 3 will have the same reference numeral but designated with a hashtag symbol (#). The configuration and operation of the embodiment of FIG. 4 is essentially the same as in FIG. 3 with these exceptions.

The C3 pyrolyzed stream in the net second depropanizer overhead line 96 # and the net stripped dehydrogenation stream in the stripping bottoms line 42" are prefractionated in the prefractionation C3 splitter column 150 # together. In an embodiment, the net second depropanizer overhead line 96 # is fed to the prefractionation column at an elevation above the feed of the net stripped dehydrogenation stream in the stripping bottoms line 42" to the column. Instead of fractionating the net main C3 stream in line 141 # it may be added to the net propane recycle stream in line 127 # to provide a common net propane recycle stream to be dehydrogenated in the paraffin dehydrogenation reactor 14. Both columns 150 # and 120" produce net bottom streams of very little propylene, so the common net propane recycle stream formed by adding the net main C3 stream in line 141 # to the net propane recycle stream in line 127 # comprises essentially propane.

EXAMPLE

We conducted a cost analysis for a conventional process in which a multistage cascade refrigeration system utilizing ethylene and propylene refrigeration loops for pyrolysis and dehydrogenation recovery including a methane compressor for pyrolysis recovery and compared it to an integrated process employing a mixed refrigerant compressor for both dehydrogenation and pyrolysis with propylene refrigeration for pyrolysis. The integrated case also employed a methane compressor, an off-gas compressor, a PSA feed gas compressor and a turbo-expander. The analysis was performed for a 500 kiloton propylene per annum dehydrogenation unit and a 500 kiloton propylene and 1500 kiloton ethylene per annum pyrolysis unit.

We found the integrated process reduced compressor power by over 7% resulting in a $9 to 12M/year reduction in utility cost which is about 8 to about 11% of the base case.

Operational savings from the integration are shown in Table 1.

TABLE 1

| Operational Expense | Savings per year ($) | Utility |
|---|---|---|
| Utility Cost | 9-12M | |
| Carbon Dioxide Emission | 7M | 70 kilometric tons/year |
| Cooling Water | | 100 $m^3/h$ |

Capital expense savings provided by the integrated process versus the base process are shown in Table 2.

TABLE 2

| Equipment | Base Process | Integrated Process |
|---|---|---|
| Drums | 21 | 9 |
| Compressor stages | 11 | 8 |

TABLE 2-continued

| Equipment | Base Process | Integrated Process |
|---|---|---|
| Expanders | 0 | 1 |
| Plate Heat Exchangers | 10 | 4 |
| Shell and Tube and Air Cooler Heat Exchangers | 14 | 7 |
| Total | 56 | 29 |

It was unexpected that equipment count by integration could be cut by almost half. Capital expense was reduced by $44M which is about 18% of the base case.

SPECIFIC EMBODIMENTS

While the following is described in conjunction with specific embodiments, it will be understood that this description is intended to illustrate and not limit the scope of the preceding description and the appended claims.

A first embodiment of the disclosure is a process for cooling streams comprising compressing a refrigerant stream to provide a compressed refrigerant stream; and heat exchanging the compressed refrigerant stream with a deethanizer reboil stream from a deethanizer column to cool the compressed refrigerant stream and provide a cooled compressed refrigerant stream and boil up the deethanized reboil stream and provide a boiling deethanizer reboil stream. An embodiment of the disclosure is one, any or all of prior embodiments in this paragraph up through the first embodiment in this paragraph wherein the deethanized reboil stream is a deethanized bottom stream and the compressed refrigerant stream is a first compressed refrigerant stream and further comprising compressing a cooled first compressed refrigerant stream to provide a second compressed refrigerant stream and heat exchanging a deethanizer side stream from the deethanizer column with the second compressed refrigerant stream to cool the second compressed refrigerant stream and provide a cooled second compressed refrigerant stream and boil up the deethanizer side stream to provide a boiling deethanizer side stream. An embodiment of the disclosure is one, any or all of prior embodiments in this paragraph up through the first embodiment in this paragraph wherein the deethanized reboil stream is a deethanized side stream, the refrigerant stream is a cooled first compressed refrigerant stream and the compressed refrigerant stream is a second compressed refrigerant stream and further comprising compressing a preliminary refrigerant stream to provide a first compressed refrigerant stream and heat exchanging a deethanizer bottoms stream from the deethanizer column with the first compressed refrigerant stream to cool the first compressed refrigerant stream and provide the cooled first compressed refrigerant stream and boil up the deethanizer side bottom to provide a boiling deethanizer bottom stream. An embodiment of the disclosure is one, any or all of prior embodiments in this paragraph up through the first embodiment in this paragraph further comprising heat exchanging the cooled second compressed refrigerant stream with a pyrolyzed stream to provide the refrigerant stream and a cooled pyrolyzed stream. An embodiment of the disclosure is one, any or all of prior embodiments in this paragraph up through the first embodiment in this paragraph further comprising boiling up a demethanized reboil bottoms stream by heat exchange with a demethanizer feed stream to provide a demethanized reboiling stream fed back to the demethanizer column and a preheated demethanizer feed stream. An embodiment of the disclosure is one, any or all of prior embodiments in this paragraph up through the first embodiment in this paragraph further comprising heat exchanging a demethanizer bottom stream with a demethanizer feed stream to cool a demethanizer feed stream and heating the demethanizer bottom stream. An embodiment of the disclosure is one, any or all of prior embodiments in this paragraph up through the first embodiment in this paragraph further comprising reboiling a C2 splitter side stream by heat exchange with a deethanizer overhead stream. An embodiment of the disclosure is one, any or all of prior embodiments in this paragraph up through the first embodiment in this paragraph further comprising fractionating the deethanizer overhead stream to provide an C2 splitter overhead stream rich in ethylene, a C2 splitter bottom stream rich in ethane and the C2 splitter side stream. An embodiment of the disclosure is one, any or all of prior embodiments in this paragraph up through the first embodiment in this paragraph further comprising compressing a propylene refrigerant in a first propylene compressor to provide a first compressed propylene refrigerant stream and boiling up a reboil C2 splitter bottom stream by heat exchange with the first compressed propylene refrigerant stream to provide a cooled first compressed propylene refrigerant stream and a reboiled C2 splitter reboiled stream. An embodiment of the disclosure is one, any or all of prior embodiments in this paragraph up through the first embodiment in this paragraph further comprising compressing the cooled first compressed propylene refrigerant stream in a second propylene compressor to provide a second compressed propylene refrigerant stream and heating an ethylene product stream by heat exchange with the second compressed propylene refrigerant stream to provide a heated and vaporized ethylene product stream and a cooled second compressed propylene refrigerant stream. An embodiment of the disclosure is one, any or all of prior embodiments in this paragraph up through the first embodiment in this paragraph further comprising expanding the cooled second compressed propylene refrigerant stream to provide an expanded cooled second compressed propylene refrigerant stream and heat exchanging the expanded cooled second compressed propylene refrigerant stream with a C2 splitter overhead stream to condense the C2 splitter overhead stream.

A second embodiment of the disclosure is a process for cooling streams comprising compressing a refrigerant stream to provide a first compressed refrigerant stream; and heat exchanging the first compressed refrigerant stream with a bottoms deethanizer reboil stream from a deethanizer column to cool the first compressed refrigerant stream and provide a cooled first compressed refrigerant stream and boil up the deethanized reboil stream and provide a boiling deethanizer reboil stream; compressing the cooled first compressed refrigerant stream in a second compressor to provide a second compressed refrigerant stream and heat exchanging a deethanizer side stream from the deethanizer column with the second compressed refrigerant stream to cool the second compressed refrigerant stream and provide a cooled second compressed refrigerant stream and boil up the deethanizer side stream to provide a boiling deethanizer side stream. An embodiment of the disclosure is one, any or all of prior embodiments in this paragraph up through the second embodiment in this paragraph further comprising heat exchanging the cooled second compressed refrigerant stream with a pyrolyzed stream to provide the refrigerant stream and a cooled pyrolyzed stream. An embodiment of the disclosure is one, any or all of prior embodiments in this paragraph up through the second embodiment in this paragraph further comprising boiling up a demethanized reboil bottoms stream by heat exchange with a demethanizer feed stream to provide a demethanized reboiling stream that is fed back to the demethanizer column and a preheated demethanizer feed stream. An embodiment of the disclosure is one, any or all of prior embodiments in this paragraph up through the second embodiment in this paragraph further comprising heat exchanging a demethanizer bottom stream with a demethanizer feed stream to cool a demethanizer feed stream and heating the demethanizer bottom stream. An embodiment of the disclosure is one, any or all of prior embodiments in this paragraph up through the second embodiment in this paragraph further comprising reboiling a C2 splitter side stream by heat exchange with a deethanizer overhead stream and fractionating the deethanizer overhead stream to provide an C2 splitter overhead stream rich in ethylene, a C2 splitter bottom stream rich in ethane and the C2 splitter side stream. An embodiment of the disclosure is one, any or all of prior embodiments in this paragraph up through the second embodiment in this paragraph further comprising compressing a propylene refrigerant in a first propylene compressor to provide a first compressed propylene refrigerant stream and boiling up a reboil C2 splitter bottom stream by heat exchange with the first compressed propylene refrigerant stream to provide a cooled first compressed propylene refrigerant stream and a reboiled C2 splitter reboiled stream. An embodiment of the disclosure is one, any or all of prior embodiments in this paragraph up through the second embodiment in this paragraph further comprising compressing the cooled first compressed propylene refrigerant stream in a second propylene compressor to provide a second compressed propylene refrigerant stream and heating an ethylene product stream by heat exchange with the second compressed propylene refrigerant stream to provide a heated ethylene-product stream and a cooled second compressed propylene refrigerant stream. An embodiment of the disclosure is one, any or all of prior embodiments in this paragraph up through the second embodiment in this paragraph further comprising expanding the cooled second compressed propylene refrigerant stream to provide an expanded cooled second compressed propylene refrigerant stream and heat exchanging the expanded cooled second compressed propylene refrigerant stream with a C2 splitter overhead stream to condense the C2 splitter overhead stream.

A third embodiment of the disclosure is an apparatus for cooling streams comprising a deethanizer bottoms reboil exchanger in downstream communication with a first compressor and a second compressor in downstream communication with the first compressor and a side reboil exchanger in downstream communication with the second compressor.

Without further elaboration, it is believed that using the preceding description that one skilled in the art can utilize the present disclosure to its fullest extent and easily ascertain the essential characteristics of this disclosure, without departing from the spirit and scope thereof, to make various changes and modifications of the disclosure and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for cooling streams comprising:

compressing a refrigerant stream to provide a compressed refrigerant stream;

heat exchanging said compressed refrigerant stream with a deethanizer reboil stream from a deethanizer column to cool the compressed refrigerant stream and provide a cooled compressed refrigerant stream and boil up said deethanized reboil stream and provide a boiling deethanizer reboil stream;

compressing a propylene refrigerant in a first propylene compressor to provide a first compressed propylene refrigerant stream and boiling up a reboil C2 splitter bottom stream by heat exchange with said first compressed propylene refrigerant stream to provide a cooled first compressed propylene refrigerant stream and a reboiled C2 splitter reboiled stream; and compressing said cooled first compressed propylene refrigerant stream in a second propylene compressor to provide a second compressed propylene refrigerant stream and heating an ethylene product stream by heat exchange with said second compressed propylene refrigerant stream to provide a heated ethylene product stream and a cooled second compressed propylene refrigerant stream.

2. The process of claim 1 wherein said deethanized reboil stream is a deethanized bottom stream and said compressed refrigerant stream is a first compressed refrigerant stream and further comprising compressing a cooled first compressed refrigerant stream to provide a second compressed refrigerant stream and heat exchanging a deethanizer side stream from said deethanizer column with said second compressed refrigerant stream to cool the second compressed refrigerant stream and provide a cooled second compressed refrigerant stream and boil up said deethanizer side stream to provide a boiling deethanizer side stream.

3. The process of claim 1 wherein said deethanized reboil stream is a deethanized side stream, said refrigerant stream is a cooled first compressed refrigerant stream and said compressed refrigerant stream is a second compressed refrigerant stream and further comprising compressing a preliminary refrigerant stream to provide a first compressed refrigerant stream and heat exchanging a deethanizer bottoms stream from said deethanizer column with said first compressed refrigerant stream to cool the first compressed refrigerant stream and provide said cooled first compressed refrigerant stream and boil up said deethanizer side bottom to provide a boiling deethanizer bottom stream.

4. The process of claim 2 further comprising heat exchanging the cooled second compressed refrigerant stream with a pyrolyzed stream to provide said refrigerant stream and a cooled pyrolyzed stream.

5. The process of claim 1 further comprising boiling up a demethanized reboil bottoms stream by heat exchange with a demethanizer feed stream to provide a demethanized reboiling bottom stream fed back to a demethanizer column and a precooled demethanizer feed stream.

6. The process of claim 1 further comprising heat exchanging a demethanizer side stream with a demethanizer feed stream to cool a demethanizer feed stream and heating said demethanizer side stream.

7. The process of claim 1 further comprising reboiling a C2 splitter side stream by heat exchange with a deethanizer overhead stream.

8. The process of claim 7 further comprising fractionating said deethanizer overhead stream to provide an C2 splitter overhead stream rich in ethylene, a C2 splitter bottom stream rich in ethane and said C2 splitter side stream.

9. The process of claim 1 further comprising expanding said cooled second compressed propylene refrigerant stream to provide an expanded cooled second compressed propylene refrigerant stream and heat exchanging said expanded cooled second compressed propylene refrigerant stream with a C2 splitter overhead stream to condense said C2 spitter overhead stream.

10. A process for cooling streams comprising:

compressing a refrigerant stream to provide a first compressed refrigerant stream;

heat exchanging said first compressed refrigerant stream with a bottoms deethanizer reboil stream from a deethanizer column to cool the first compressed refrigerant stream and provide a cooled first compressed refrigerant stream and boil up said deethanized reboil stream and provide a boiling deethanizer reboil stream;

compressing said cooled first compressed refrigerant stream in a second compressor to provide a second compressed refrigerant stream and heat exchanging a deethanizer side stream from said deethanizer column with said second compressed refrigerant stream to cool the second compressed refrigerant stream and provide a cooled second compressed refrigerant stream and boil up said deethanizer side stream to provide a boiling deethanizer side stream;

compressing a propylene refrigerant in a first propylene compressor to provide a first compressed propylene refrigerant stream and boiling up a reboil C2 splitter bottom stream by heat exchange with said first compressed propylene refrigerant stream to provide a cooled first compressed propylene refrigerant stream and a reboiled C2 splitter reboiled stream; and compressing said cooled first compressed propylene refrigerant stream in a second propylene compressor to provide a second compressed propylene refrigerant stream and heating an ethylene product stream by heat exchange with said second compressed propylene refrigerant stream to provide a heated ethylene product stream and a cooled second compressed propylene refrigerant stream.

11. The process of claim 10 further comprising heat exchanging the cooled second compressed refrigerant stream with a pyrolyzed stream to provide said refrigerant stream and a cooled pyrolyzed stream.

12. The process of claim 10 further comprising boiling up a demethanized reboil bottoms stream by heat exchange with a demethanizer feed stream to provide a demethanized reboiling stream that is fed back to a demethanizer column and a precooled demethanizer feed stream.

13. The process of claim 10 further comprising heat exchanging a demethanizer bottom stream with a demethanizer feed stream to cool a demethanizer feed stream and heating said demethanizer bottom stream.

14. The process of claim 10 further comprising reboiling a C2 splitter side stream by heat exchange with a deethanizer overhead stream and fractionating said deethanizer overhead stream to provide an C2 splitter overhead stream rich in ethylene, a C2 splitter bottom stream rich in ethane and said C2 splitter side stream.

15. The process of claim 10 further comprising expanding said cooled second compressed propylene refrigerant stream to provide an expanded cooled second compressed propylene refrigerant stream and heat exchanging said expanded cooled second compressed propylene refrigerant stream with a C2 splitter overhead stream to condense said C2 spitter overhead stream.

16. An apparatus for cooling streams comprising:

a deethanizer bottoms reboil exchanger in downstream communication with a first compressor;

a second compressor in downstream communication with said first compressor;

a side reboil exchanger in downstream communication with said second compressor;

a dehydrogenation cold box in downstream communication with said first compressor, wherein said dehydrogenation cold box is configured to receive a compressed refrigerant stream from said first compressor and to cool a dehydrogenated hydrocarbon stream by heat exchange with said compressed refrigerant stream, and a pyrolysis cold box in downstream communication with said second compressor, wherein said pyrolysis cold box is configured to receive a second compressed refrigerant stream from said second compressor and to cool said second compressed refrigerant stream by heat exchange with a pyrolyzed hydrocarbon stream, wherein the first compressor, the deethanizer bottoms reboil exchanger, the second compressor, the side reboil exchanger, the dehydrogenation cold box, and the pyrolysis cold box together are arranged to circulate a single refrigerant stream through each of said units.

* * * * *